United States Patent [19]

Gruetzmacher et al.

[11] 4,251,563
[45] Feb. 17, 1981

[54] COMPOSITIONS CONTAINING N-NITROSAMINE FORMATION OR OXIDATION INHIBITORS AND THE USE THEREOF

[75] Inventors: Gordon D. Gruetzmacher, Gales Ferry; Leonard J. Czuba, New London, both of Conn.

[73] Assignee: Pfizer Inc., New York, N.Y.

[21] Appl. No.: 20,883

[22] Filed: Mar. 15, 1979

[51] Int. Cl.³ .................... A23D 5/00; A61K 31/375
[52] U.S. Cl. ................................... 426/605; 424/280
[58] Field of Search ........................ 424/280; 426/605

[56] References Cited

U.S. PATENT DOCUMENTS

| 2,383,816 | 8/1945 | Riemenschneider et al. .... 260/398.5 |
| 2,440,383 | 4/1948 | Riemenschneider et al. .... 260/399.5 |

OTHER PUBLICATIONS

Chem. Abstr., 75, #25253w, (1971), 80, #36050g, (1974), 84#72744c, (1976).
Cort. J. Am. Oil Chem. Soc., 51:321-325, (1974), 88#491669, (1978).
Sen et al., Food Cosmet. Toxicol., 14:167-170, (1976).
Fan et al., Food Cosmet. Tox., 15:423-431, (1977).
Fiddler et al., J. Ag. Food Chem., 26:653-656, (1978).
Sen et al., J. As. Food Chem., 24:397-401, (1976).
Pensabene et al., J. Food Sci., 43:801-802, (1978).
Pensabene et al., J. Food Sci., 41:199-200, (1976).
Motram et al., J. Sci. Ed. Agric., 28:352-355, 1977.
Walters et al., Z Leb. Unt. For., 162:372-385, (1976).

*Primary Examiner*—Shep K. Rose
*Attorney, Agent, or Firm*—Francis X. Murphy; Charles J. Knuth; Paul D. Thomas

[57] ABSTRACT

Compositions of nitrite preserved food, emulsified preparations, breakfast cereal or food premixes and erythorbyl or ascorbyl laurate or erythorbyl caprate show substantial inhibition of potentially harmful or objectionable degradation arising from N-nitrosamine formation or oxidation.

6 Claims, No Drawings

COMPOSITIONS CONTAINING N-NITROSAMINE FORMATION OR OXIDATION INHIBITORS AND THE USE THEREOF

BACKGROUND OF THE INVENTION

This invention relates to compositions containing erythorbyl or ascorbyl laurate or erythorbyl caprate which inhibit N-nitrosamine formation or oxidation and to methods of achieving inhibition in such compositions.

Nitrites are used as preservatives and curatives in food but this use has recently been found to cause N-nitrosamine formation. It is thought that these potent compounds are produced during cooking and are derived from the amines and amine precursors such as amino acids, proteins, nucleic acids, phospholipids and quaternary ammonium compounds present in the food. However, elimination of the causative agent, nitrite, from the food seems to be unwarranted because it prolongs shelf life, prevents spoilage and produces a desirable red color and cured flavor.

Nitrosamine formation also takes place in dermal cremes that contain such ingredients as triethylamine, triethanolamine, glycerolamine, amino acids, proteins and other amine derivatives (T. Y. Fan, et. al., *Food and Cosmet Tox.*, 15, 423 (1977). The process of formation of the N-nitrosamines in this instance is not known. Obvious agents such as nitrite are not present. Nevertheless, potential exposure to N-nitrosamines exists.

Compounds such as ascorbic and erythorbic acid, phenolic derivatives such as BHA, BHT, TBHQ and alkyl gallates, tocopherols, gum guaiac and nordihydroguaiaretic acid have been studied as inhibitors of harmful or objectionable degradation arising from N-nitrosamine formation. In addition, their use also provides the advantage of their well-known capacity to inhibit oxidation. (W. Fiddler, et. al., *Food Chem.*, 26, 653 (1978); D. Mottram, et. al., *J. Sci. Fd. Agric.*, 28, 352 (1977); J. W. Pensabene, et. al., *J. Food Sci.*, 41, 199 (1976); N. Sen, et. al., *J. Ag. Food Chem.*, 24, 397 (1976); N. Sen et. al., *Food Cosmet. Toxicol.*, 14, 167 (1976); J. Pensabene, et. al., *J. Food Sci.*, 43, 801 (1978); C. L. Walters, et. al., *Z. Lebensm. Unters Forsch*, 162, 377 (1976); U.S. Pat. No. 2,159,986; U.S. Pat. No. 2,408,897; U.S. Pat. No. 2,440,383; U.S. Pat. No. 2,383,816; U.S. Ser. No. 861,506). However, nitrite preserved food, such as bacon and salami, emulsified preparations such as dermal cremes, soap and shampoo, food preparations such as mayonnaise and salad dressing, and breakfast cereal are two phase systems having sensitive ingredients in both phases and most of the compounds studied are only soluble in one phase. Consequently, they do not produce the desired inhibition.

It now has been surprisingly discovered that the two phase compositions of the invention which contain erythorbyl or ascorbyl laurate or erythorbyl caprate show substantial inhibition of N-nitrosamine formation or oxidation.

SUMMARY OF THE INVENTION

The compositions of the present invention include a nitrite preserved food composition, an emulsified composition and a breakfast cereal or food premix composition each contaning erythorbyl or ascorbyl laurate or erythorbyl caprate. The nitrite preserved food composition is a combination of a nitrite preserved food containing amines, amino acids, proteins, nucleic acids, phospholipids or quaternary ammonium compounds that are capable of forming N-nitrosamines and the laurate or caprate in an amount sufficient to inhibit N-nitrosamine formation. The emulsified composition is a combination of an emulsified preparation containing amines, hydroxy amines, amino acids, proteins, phospholipids or quaternary ammonium compounds that are capable of forming N-nitrosamines and the laurate or caprate in an amount sufficient to inhibit N-nitrosamine formation, or is a combination of an emulsified preparation containing oxidizable ingredients and the laurate or caprate in an amount sufficient to inhibit oxidation. The breakfast cereal or food premix composition is a combination of a breakfast cereal or food premix containing oxidizable ingredients and the laurate or caprate in an amount sufficient to inhibit oxidation.

The methods of the present invention include inhibition of N-nitrosamine formation in a nitrite preserved food and in an emulsified preparation and inhibition of oxidation in an emulsified preparation and a breakfast cereal or food premix. The methods involve combining the food, preparation, cereal or food premix with an inhibitory amount of erythorbyl or ascorbyl laurate or erythorbyl caprate.

Preferred nitrite preserved food compositions and preferred methods of inhibiting N-nitrosamine formation in nitrite preserved food include those wherein the food is bacon and wherein the amount of laurate or caprate is from about 0.001% to about 0.3% by weight relative to the total weight of the food.

Preferred emulsified compositions and preferred methods of inhibiting N-nitrosamine formation or oxidation in an emulsified preparation include those wherein the preparation is dermal creme, soap or shampoo; wherein the preparation is a prepared food product and wherein the amount of laurate or caprate is from about 0.001% to about 0.3% by weight relative to the total weight of the composition.

A preferred breakfast cereal or food premix composition and a preferred method of inhibiting oxidation in a breakfast cereal or food premix include those wherein the amount of laurate or caprate is from about 0.001% to about 0.3% by weight relative to the total weight of the cereal.

Another preferred method of inhibiting N-nitrosamine formation or oxidation is an emulsified preparation is one wherein the laurate or caprate is combined with the individual ingredients of the preparation that are capable of forming N-nitrosamines or being oxidized.

Especially preferred compositions and methods include those wherein erythorbyl laurate is used.

DETAILED DESCRIPTION OF THE INVENTION

The compositions of the invention exhibit substantial inhibition of the formation of harmful or objectionable degradation products arising from N-nitrosation or oxidation of their sensitive ingredients. They exist as two phases, for example, natural fat and aqueous, oil and water, or oil and dry solids, which possess contrasting physical characteristics and are immiscible. Nevertheless, inhibition occurs in both phases because the laurate or caprate is equally distributed at a high concentration between them.

The nitrite preserved food used in the food composition includes meat, processed meat, meat mixtures, sausage, bologna, salami, bacon, frankfurters, deviled ham, deviled beef, canned ham, canned beef, jellied pork and beef, corned beef, corned beef hash, smoked ham, smoked pork, fresh ham, cured pork, barbecue sauce, spaghetti sauce with meat, pickled beef, pickled pork, cured meat and other types of food to which has been added a nitrite preservative.

The emulsified preparations used in the emulsified composition include dermal or hair creme preparations for external use, soap, hair dressing, all types of ointments, bath oil, perfume, shampoo, hand creme, cleansing creme, vanishing creme, foundation creme, all-purpose creme, hormone creme, sunscreen creme, antiperspirant creme, cold wave creme as well as prepared food products such as mayonnaise, salad dressing, dairy products such as margarine, butter, buttered syrup and cheese and the like.

The breakfast cereal compositions contain the laurate or caprate in both the oil and dry phases of the breakfast cereal. It is prepared by combining the laurate or caprate and the cereal in the wet processing stage so that the laurate or caprate distributes between the oil and wet portions of the cereal. It can also be prepared by applying to the finished cereal an aqueous solution or suspension of the laurate or caprate. Their interphase mobility facilitates their migration to both phases of the cereal. If a wet mixture is used, it is then flaked, popped or extruded and dried to produce the dry, solid composition.

The food premixes used in the food premix compositions include cake mixes, cookie mixes, pancake mixes, biscuit mixes, pizza dough mixes, pie dough mixes and similar mixes which contain oil or fat and dry phases. Like the application to a breakfast cereal composition, the food premix composition is prepared by combining the laurate or caprate and the food premix in the wet mixing stage or they may be applied to the finished mix to take advantage of their interphase mobility.

The inhibitory agents are the lauric acid esters of erythorbic acid and ascorbic acid and the caproic acid ester of erythorbic acid. Their preparations are well known in the art. For example, preparation using concentrated sulfuric acid is disclosed in U.S. Pat. No. 2,408,897.

In general, the characteristics of the agents that are essential to the invention and impart the inhibitory quality to the compositions are their approximately even distribution and their high solubility in the two phases of the compositions. As illustrated by Example 7, their distribution coefficient between an ideal two phase system, oil and water, is approximately 1 and they exhibit high solubility (total solubility) at their useful level of inhibition. These characteristics are conveyed to the composition and permit substantial inhibition of harmful or objectionable degradation.

Other types of similar compounds do not exhibit even distribution and high total solubility in the ideal system and would not produce inhibition in both phases of the compositions. For example, compounds such as BHA, BHT, TBHQ, tocopherols and alkyl gallates are water-insoluble meaning that their distribution coefficients (oil/water) are essentially infinity. Compounds such as erythorbic or ascorbic acid, their alkali metal salts, and others are oil-insoluble. Moreover, fatty acid esters other than erythorbic caprate or the laurates of the invention exhibit undesirable distribution coefficients and solubilities. As shown by Example 7, while ascorbyl palmitate has a distribution coefficient of 1.7, it has low total solubility and while ascorbyl caprate has high total solubility, it has a very low distribution coefficient. The combination of these values makes these esters ineffective inhibitors.

The preparation of the nitrite preserved food composition follows well-known methods for making such foods as bacon, bologna and the others indicated above. In general, the laurate or caprate is combined with the food during its preparation. Alternatively, the laurate or caprate may be added to the food after it has been cured with nitrite. Using either method, the laurate or caprate does not interfere with the slow curing reaction of nitric oxide and heme that produces the characteristic pink color and cured meat flavor of such food. In addition, if desired, an appropriate amount of the sodium salt of erythorbic or ascorbic acid may be used in the preparation of the food in order to promote curing. When preparing pickled meats such as bacon, the laurate or caprate is usually added to the pickle solution which is then combined with the meat. The usual amount of laurate or caprate sufficient to substantially inhibit the formation of N-nitrosamines in the food composition is about 0.001% to 0.3% as indicated above.

The preparation of the emulsified composition follows well-known methods for making emulsified preparations for external use and prepared food products. Combinations of the ingredients of the preparations using a variety of amounts and formulations are multitudinous. Most applications mentioned are based upon art accepted recipes. For example, H. W. Hibbott describes a variety of dermal creme, dressing, hair creme, cosmetic, antiperspirant, soap, shampoo, and perfume preparations and formulations in "Handbook of Cosmetic Science", the MacMillan Co., New York, 1963. The laurate or caprate and the preparation are usually combined during formation of the emulsion or the laurate or caprate may be premixed with the sensitive ingredients which will be used in the preparation. In addition to the ingredients composed of compounds capable of forming N-nitrosamines as indicated above, the ingredients may also be composed of compounds sensitive to oxidation. These include natural and synthetic, olefinic oils, waxes, acids, perfumes such as eugenol, lavender, jasmones and the like, humectants, emulsifiers, soaps, sunscreen agents, color agents, pigments, stainers, flavorings, fatty alcohols, amino alcohols, and other similar compounds. The usual amount of laurate or caprate sufficient to substantially inhibit formation of N-nitrosamines or oxidation in the emulsified composition for external use is about 0.001% to 0.3% as indicated above.

Methods for the combination of the ingredients of the prepared food product are also known. Recipes for mayonnaise, butter and cheese may be found in any text on the art. The laurate or caprate and the prepared food product are usually combined during the product's making but may also be combined afterward. The usual amount of laurate or caprate sufficient to substantially inhibit N-nitrosamine formation or oxidation in an emulsified prepared food product composition is about 0.001% to 0.3% as indicated above.

The presence or absence of the harmful or objectionable degradation products may be determined by a trained test panel using olfactory or visual senses to judge protected and control sample characteristics such as color, rancidity, and "painty" (turpentine-like), "grassy", "fishy" (amine), "tart" or astringent odors. Other methods may also be used including gas chromatographic analysis, high pressure liquid chromatography, colormetric methods and thermal energy analysis (TEA), the accepted method of testing for N-nitrosamines. Examples 1 through 6 illustrate analysis by several of these methods and demonstrate the ability of the erythorbyl or ascorbyl laurate or erythorbyl caprate to inhibit formation of N-nitrosamines or oxidation in the compositions of the invention.

The examples are illustrative of the processes used to make compositions of bacon, bologna, hand creme, emollient lotion, mayonnaise, corn flakes and erythorbyl or ascorbyl laurate or erythorbyl caprate. They in no way limit the scope of the appended claims. All formulations, emulsifications, mixing and other processes are carried out at ambient temperature unless otherwise stated.

EXAMPLE 1

Preparation and Evaluation of Bacon Pickle Solution

Preparation

Several base pickle solutions were prepared in tap water using the following proportions of ingredients: 2.0% sodium tripolyphosphate; 2.5% sucrose, 0%, 0.20% or 0.55% sodium erythorbate; 0.12% or 0.20% sodium nitrite; and 17.0% sodium chloride. Each ingredient was added to the water in the order given and completely dissolved before adding the next ingredient. The desired amount of ascorbyl or erythorbyl laurate was added to selected base solutions as follows. A dispersion or ascorbyl or erythorbyl laurate and Tween 20 was prepared by slurrying 2 parts of Tween 20 and 5 parts of ascorbyl or erythorbyl laurate, hydrating the slurry with a small amount of the base pickle solution and vigorously agitating the hydrated slurry for 10 min to break up the large agglomerates that formed. The slurry was then added to enough of the selected base solution to give the desired ascorbyl or erythorbyl laurate concentration (0.25%, 0.5%, 0.995%). The resultant mixture was homogenized 2 times at 1000 psi in a single-stage homogenizer to give the final pickle solution. The pickle solution was chilled to about 40° F. immediately after preparation and used to prepare the bacon on the day of preparation.

Bacon Preparation

Duplicate pork bellies of about 10 lbs weight were stitch-pumped using each of the various concentrations of control or laurate treated cooled, agitated pickle solutions. After they were pumped to 10% additional weight, the bellies were uniformly heated, smoked and chilled to represent normal bacon processing conditions.

The bellies were then sliced in their entirety and a representative sample sufficient to yield ½ lb of fried bacon was taken from each. The sample bacon slices were fried at 340° F. for 3 min on each side. The combined bacon slices from each belly were analyzed for dimethylnitrosamine and nitrosopyrrolidine using standard procedures and a TEA analyzer. The duplicate results for the treated, fried bacon containing the various laurate concentrations are given in the table following and are compared to null control (untreated) fried bacon containing 200 or 550 ppm sodium erythorbate and to positive control fried bacon containing 500 ppm tocopherol added as a Tween 20 slurry in pickle solution. The results show that fried bacon treated with erythorbyl or ascorbyl laurate had approximately four times less nitrosopyrrolidine than untreated fried bacon. Furthermore, the level of reduction is about the same as that achieved using tocopherol which suggests that the Tween 20 dispersant has carried the tocopherol into the water layer of the bacon.

TABLE

Production of Dimethylnitrosamine and Nitrosopyrrolidine in Treated and Untreated Fried Bacon (A) At a Level of 120 ppm (0.12%) NaNO$_2$

| NaEr[1] | EL[2] | AL[3] | TOC[4] | DMNA[5] | NPy[6] |
|---|---|---|---|---|---|
| 200[7] | — | — | — | 1.0 | 4.2 |
|  |  |  |  | 1.2 | 3.3 |
| 550[7] | — | — | — | trace | trace |
|  |  |  |  | trace | 2.3* |
| 550 | 250 | — | — | 1.2 | 2.5 |
|  |  |  |  | 1.7 | trace |
| 550 | 500 | — | — | trace | trace |
|  |  |  |  | trace | trace |
| 550 | — | 500 | — | 2.7* | 1.4 |
|  |  |  |  | 1.7 | 2.4* |
| —[8] | 995 | — | — | 1.2 | trace |
|  |  |  |  | 1.0 | none detected |
| 550[9] | — | — | 500 | 1.9* | none detected |
|  |  |  |  | trace | none detected |

(B) At a Level of 200 ppm (0.20%) NaNO$_2$

| NaEr[1] | EL[2] | AL[3] | TOC[4] | DMNA[5] | NPy[6] |
|---|---|---|---|---|---|
| 200 | — | — | — | 2.1 | 3.6 |
|  |  |  |  | 1.6 | 3.9 |
| 550 | — | — | — | 2.4 | 7.1 |
|  |  |  |  | 1.1 | 2.6 |
| 550 | 250 | — | — | 2.0* | 1.3 |
|  |  |  |  | 2.0 | trace |
| 550 | 500 | — | — | 1.3 | trace |
|  |  |  |  | 1.9 | trace |
| 550 | — | 500 | — | 1.6 | trace |
|  |  |  |  | 2.6 | 1.6 |
| —[8] | 995 | — | — | 2.2 | none detected |
|  |  |  |  | 1.7* | 1.0 |
| 550[9] | — | — | 500 | trace | none detected |
|  |  |  |  | 3.0 | 1.1 |

[1]Concentration (ppm) of sodium erythorbate (NaEr) in the bacon sample.
[2]Concentration (ppm) of erythorbyl laurate (EL) in the bacon sample.
[3]Concentration (ppm) of ascorbyl laurate (AL) in the bacon sample.
[4]Concentration (ppm) of tocopherol (TOC) in the bacon sample.
[5]Level (ppb) of dimethylnitrosamine (DMNA) detected in the fried bacon sample using thermal energy analysis. Values are + or − 20 percent unless noted by an * which means values vary less than + or − 50 percent. Trace means less than 1 ppb. Limit of detection is 0.2 ppb.
[6]Level (ppb) of nitrosopyrrolidine detected in the fried bacon sample using thermal energy analysis. Values are + or − 20 percent unless noted by an * which means values vary less than + or − 50 percent. Trace means less than 1 ppb. Limit of detection is 0.2 ppb.
[7]Null control fried bacon containing only sodium erythorbate.
[8]A fried bacon sample prepared with no sodium erythorbate and having the same concentration of erythorbyl radical as 550 ppm sodium erythorbate plus 500 ppm erythorbyl laurate.
[9]Positive control fried bacon containing tocopherol.

EXAMPLE 2

Preparation and Evaluation of Bologna

In a large mixer there are combined 60 lb of whole carcass beef which has been ground through a ¼" plate, 40 lb of regular pork trimmings which has been ground through a ⅜" plate, 2 lb 12 oz of salt, 8 oz of sugar, 4 oz of ground white pepper, 1 oz of coriander, 1 oz of mace, 0.85 oz of sodium erythorbate, 0.25 oz of sodium nitrite, and 1.00 oz of erythorbyl laurate. 25 lb of chopped ice is added and the mixture is cycled through a mechanical emulsifier until the desired texture is attained. The finished emulsion is transferred to a casing stuffer and stuffed into a No. 8 by 36 in. fibrous casing. The resultant product is ready for smoking, which will require approximately 8 hrs. The product is placed in a smokehouse at 130° F. with the damper open and cooked for 30 min. The damper is then closed and the temperature is raised 10° F./hr to 170° F. The heating is continued at 170° F. until an internal temperature of 156° F. is reached. The resultant bologna is cold showered with tap water for 35 to 40 min, held at room temperature for 30 min, and placed in a cooler at 36°–40° F. This procedure will produce bolognas of approximately 18 lb with a 15 in. circumference.

The treated bologna is sliced, wrapped and stored at 36°–40° F. for 1 month and its color, odor and flavor are compared to a similarly prepared and stored, untreated bologna. The comparison panel will find that the treated bologna has undergone substantially less objectionable change relative to the untreated bologna.

The two bolognas may be analyzed for N-nitrosamines using standard procedures and a TEA analyzer. The analysis will show that the bologna produced using erythorbyl laurate contains substantially reduced levels of N-nitrosamines relative to the untreated bologna.

EXAMPLE 3

Preparation and Evaluation of Hand Creme

A hand creme is prepared by mixing a water phase at 70° C. with an oil phase at 75° C. The oil phase consists of 2.0 g of isopropyl myristate, 2.0 g of cetyl alcohol, 15.0 g of stearic acid, 2.0 g of lanolin, and 20.0 mg of erythorbyl laurate. The water phase consists of 71.6 ml of deionized water, 3.0 g of glycerol, 3.0 g of 70% sorbitol, and 1.4 g of triethanolamine. After thoroughly mixing the oil and water phases, the emulsion is cooled to 45° C. at which time the appropriate perfumes are added and mixed thoroughly into the emulsion. After cooling the emulsion to room temperature, the resultant hand creme is placed in an opaque glass jar and sealed.

Using an accelerated stability test at 63° C. this hand creme is compared to a similarly prepared hand creme containing no erythorbyl laurate. After one month of storage at 63° C., the color, appearance and odor of both hand cremes are evaluated against freshly prepared control hand creme. The test panel will observe that the treated hand creme has undergone substantially less objectionable change relative to the untreated hand creme.

Portions of the hand cremes described above may be analyzed for N-nitrosamines using a Thermal Energy Analyzer (TEA) and standard procedures. The analysis will show that the treated hand creme has substantially reduced levels of N-nitrosamines relative to the untreated hand creme.

EXAMPLE 4

Preparation and Evaluation of an Emollient Lotion

An oil phase consisting of 70 g of mineral oil, 30 g of lanolin, and 30 g of glycerol monostearate and heated to 75° C. is added to a water phase consisting of 15 g triethanolamine, 200 mg of erythorbyl caprate, and 849 ml of water, also at 75° C. After thoroughly mixing the oil and water phases at 75° C., the emulsion is cooled to 45° C. and perfumed. After cooling to room temperature the emulsion is homogenized to give the emollient lotion.

Using the accelerated stability tests of Example 3 the treated emollient lotion is compared to a similarly prepared, untreated emollient lotion. They will show that the treated emollient lotion has undergone substantially less degradation than the untreated lotion.

EXAMPLE 5

Preparation and Evaluation of Mayonnaise

In an electric beater, 20 g of egg yolks, 1.2 g of dry mustard, 3.0 g of salt, and 10 ml of vinegar are combined and well beaten; 144 g of vegetable oil (such as cottonseed, corn, or sesame) which contains 200 ppm (0.02%) of ascorbyl or erythorbyl laurate is then added with constant whipping, and beating is continued until there is complete emulsification and no free oil remains. An additional 10 ml of vinegar is added and the beating is continued for a few minutes longer until the emulsion is smooth and of a semi-solid consistency. The resultant mayonnaise is packed in jars and capped.

After three months of storage at room temperature, the color, odor and freshness of the treated mayonnaise are evaluated against similarly stored, untreated mayonnaise and against freshly prepared mayonnaise. The tests will show that the treated mayonnaise has undergone substantially less objectionable change.

EXAMPLE 6

Preparation and Stabilization of Corn Flakes

In a cylindrical pressure cooker are placed about 1700 pounds of degermed and debranned, No. 4–5 milled, hybrid yellow corn and 36 gallons of flavoring syrup composed of sugar, malt, salt and water. The mixture is cooked at 18 psi steam pressure for about 1½ hours to produce a moisture content of about 33%. Uniform translucency of the kernels will indicate an adequate cook. The kernels are crushed and dried to about 21% moisture. The dried, crushed grits are then heat tempered at 180° F. for 16 hours in order to evenly distribute the water content. The cooked, dried grits are flaked using a conventional flake roller and are passed directly to the toasting oven where they are heated at 575° F. for 50 seconds to produce the finished flakes of less than 3% moisture content. As they cool, they are treated with an aqueous spray of B-complex vitamins and 0.005% by weight erythorbyl laurate relative to the final corn flakes weight. The treated, finished flakes are placed in paper boxes with waxed paper liners.

Treated and untreated flakes are stored six months at room temperature and then compared. The treated flakes will have an insignificant rancid and painty taste relative to untreated flakes.

Similar results will be obtained when the erythorbyl laurate is mixed with the flavoring syrup and the mixture added to the milled corn before cooking.

EXAMPLE 7

Determination of Equilibrium Oil-Water Solubility (PPM) and Phase Distribution Coefficient The equilibrium oil-water solubility was determined by stirring 1.00 g of the test esters overnight with a mixture of 100 ml of vegetable oil and 100 ml of water. The oil and water layers were separated by centrifugation at 10,000 rpm for 30 min. Any undissolved ester was removed by gravity filtration through fluted filter paper. The oil and water layers were assayed for ester using 0.01N $I_2$ solution. The following table summarizes the results.

| Equilibrium Oil-Water Solubility (PPM) And Phase Distribution Coefficient | | | | |
|---|---|---|---|---|
| Erythorbyl Caprate | Ascorbyl Caprate | Erythorbyl Laurate | Ascorbyl Laurate | Ascorbyl Palmitate |
| Oil Phase Solubility (ppm) | | | | |
| 1500 | 100 | 450 | 250 | 110 |
| Water Phase Sol- | | | | |

-continued

| | Equilibrium Oil-Water Solubility (PPM) And Phase Distribution Coefficient | | | | |
|---|---|---|---|---|---|
| | Erythorbyl Caprate | Ascorbyl Caprate | Erythorbyl Laurate | Ascorbyl Laurate | Ascorbyl Palmitate |
| ubility (ppm) | 2500 | 5300 | 350 | 140 | 65 |
| Total Solubility (ppm) | 4000 | 5400 | 700 | 390 | 175 |
| $K_D$ | 0.6 | 0.02 | 1.3 | 1.8 | 1.7 |

We claim:

1. A method of inhibiting N-nitrosamine formation in an emulsified preparation, which comprises:
   combining the preparation containing amines, hydroxy amines, amino acids, proteins, phospholipids or quaternary ammonium compounds that are capable of forming N-nitrosamines and
   an inhibitory amount of erythorbyl or ascorbyl laurate or erythorbyl caprate.

2. A method of inhibiting oxidation in an emulsified preparation, which comprises:
   combining the preparation containing oxidizable ingredients and
   an inhibitory amount of at least 200 ppm or erythorbyl or ascorbyl laurate or erythorbyl caprate.

3. A method of claim 1 or 2 wherein the laurate or caprate is combined with the individual ingredients of the preparation that are capable of forming N-nitrosamines or being oxidized.

4. A method of claim 1 or 2 wherein the preparation is a prepared food product.

5. A method of claim 1 or 2 wherein the amount is from about 0.002% to about 0.3% by weight relative to the total weight of the preparation.

6. A method of claim 1 or 2 wherein the preparation is mayonnaise.

* * * * *